United States Patent
McNair

(10) Patent No.: US 11,810,652 B1
(45) Date of Patent: *Nov. 7, 2023

(54) COMPUTER DECISION SUPPORT FOR DETERMINING SURGERY CANDIDACY IN STAGE FOUR CHRONIC KIDNEY DISEASE

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

( * ) Notice: Subject to any disclaimer, the term of this patent is extended or adjusted under 35 U.S.C. 154(b) by 541 days.

This patent is subject to a terminal disclaimer.

(21) Appl. No.: 17/009,459

(22) Filed: Sep. 1, 2020

Related U.S. Application Data

(63) Continuation of application No. 15/144,378, filed on May 2, 2016, now Pat. No. 10,796,802.

(60) Provisional application No. 62/155,629, filed on May 1, 2015.

(51) Int. Cl.
*G16H 50/30* (2018.01)
*G16H 10/60* (2018.01)
*G06Q 10/1093* (2023.01)

(52) U.S. Cl.
CPC ......... *G16H 50/30* (2018.01); *G06Q 10/1097* (2013.01); *G16H 10/60* (2018.01)

(58) Field of Classification Search
None
See application file for complete search history.

(56) References Cited

U.S. PATENT DOCUMENTS

| | | | | |
|---|---|---|---|---|
| 2009/0156924 A1* | 6/2009 | Shariati | ................. | G16H 20/00 600/365 |
| 2010/0125241 A1* | 5/2010 | Prud'homme | ......... | G16H 20/17 600/300 |
| 2012/0020460 A1* | 1/2012 | Witten | ................... | A61N 5/103 378/65 |
| 2013/0144642 A1 | 6/2013 | Bessette | | |
| 2014/0278492 A1* | 9/2014 | Silver | .................... | G16H 50/20 705/2 |

(Continued)

OTHER PUBLICATIONS

Lebov, J. F. (2014). Pesticide exposure and end-stage renal disease among pesticide applicators and their spouses in the agricultural health study (Order No. 3634017). Available from ProQuest Dissertations and Theses Professional. (1612598536). (Year: 2014).*

*Primary Examiner* — Robert A Sorey
(74) *Attorney, Agent, or Firm* — Invoke

(57) ABSTRACT

Systems, methods and computer-readable media are provided for predicting candidacy for Kidney Surgery and related computer-performed decision support. In particular, embodiments of the disclosure are directed to identifying populations of patients who are candidates for vascular access placement in Chronic Kidney Disease (CKD). Some embodiments of the present disclosure provide a system and method for continually tracking the clinical and physiologic status of a patient in a hospital. At least some of the embodiments assist nephrologists in preventing and reducing the frequency of crises in urgent/emergent presentation with requirement for dialysis ("crashing onto dialysis") by using the systems' capability to recognize patterns in a patient's eGFR and serum uric acid values before the patient deteriorates or reaches a crisis.

23 Claims, 8 Drawing Sheets

(56) References Cited

U.S. PATENT DOCUMENTS

| | | |
|---|---|---|
| 2015/0193583 A1 | 7/2015 | McNair et al. |
| 2015/0220698 A1 | 8/2015 | Argyropoulos et al. |
| 2016/0206597 A1* | 7/2016 | Bransford ................ A61P 9/08 |
| 2016/0291036 A1 | 10/2016 | O'Bryant |
| 2017/0115310 A1* | 4/2017 | Colhoun ................ G16H 50/30 |
| 2017/0124269 A1 | 5/2017 | McNair et al. |
| 2017/0228507 A1 | 8/2017 | Bottinger et al. |
| 2017/0290551 A1 | 10/2017 | An et al. |

\* cited by examiner

| ITEM | VALUE |
|---|---|
| SENSITIVITY | 92% |
| SPECIFICITY | 83% |
| EVENT PREVALENCE | 34% |
| POSITIVE PREDICTIVE VALUE (PPV) | 73% |
| NEGATIVE PREDICTIVE VALUE (NPV) | 95% |

```
############################################################################

# CERDSM - CERDSM - CKD progression from first eGFR < 19 to eGFR 6

###################################################################### esrd <- read.csv(file="c:/0_cerdsm/0__math_models/7_nephrology/CKD/
dsm_egfr_lt_19_3_90.csv", header=TRUE,
       colClasses=rep("numeric",5))
case, uric_gt_7, allopur, egfr_sl_gt_14, t_to_egfr6_lt_180 fit1 <- glm(t_to_egfr6_lt_180 ~ uric_gt_7 + allopur + egfr_sl_gt_14, family="binomial", data=esrd)
summary(fit1)
#               Estimate Std. Error z value Pr(>|z|)
# (Intercept)   -3.22503   1.41660  -2.277  0.02281 *
# uric_gt_7     -0.02967   1.08987  -0.027  0.97829
# allopur        0.79209   1.31409   0.603  0.54666
# egfr_sl_gt_14  4.12228   1.26124   3.268  0.00108 **

#     Null deviance: 45.004  on 34  degrees of freedom
# Residual deviance: 24.950  on 31  degrees of freedom
AIC: 32.95 fit2 <- glm(t_to_egfr6_lt_180 ~ egfr_sl_gt_14, family="binomial", data=esrd)
summary(fit2)
#               Estimate Std. Error z value Pr(>|z|)
# (Intercept)   -2.944     1.026    -2.870  0.004104 **
# egfr_sl_gt_14  3.956     1.180     3.351  0.000804 ***

#     Null deviance: 45.004  on 34  degrees of freedom
# Residual deviance: 25.338  on 33  degrees of freedom
AIC: 29.34 library(pROC)

ds4 <- read.csv(file="c:/0_cerdsm/0__math_models/7_nephrology/CKD/roc.csv")
roc1 <- roc(ds4[,1] ~ ds4[,2], percent=TRUE,
# arguments for auc
# partial.auc=c(100, 90), partial.auc.correct=TRUE,
#  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")
# AUC = 89% (78-100)

# calculate significance (column-major)
x2 <- matrix(c(11,1,4,19), nrow=2)
fisher.test(x2, alternative="two.sided")

# sensitivity = 92% (83-100)
# specificity = 83% (70-95)
# prevalence  = 34% (19-50)
# PPV = 73% (59-88)
# NPV = 95% (88-100)
# OR = 44.0
# Fisher chi-sq p-value = 3.3e-05.
```

*FIG. 4A*

```
###########################################################################

# CERDSM - Particle Swarm Solver for Hankel Matrix Representation of Short Time Series

###########################################################################
library(pso)

# initialization
# passing NA in e or y[3,3] throws error
# e <- c(-0.0316,0.0003,0.0957,-0.002)    # soln.1
# e <- c(-1.4675,-1.1130,-0.7749,-0.8274) # soln.2
# e <- runif(4)  # may not converge
e <- rep(0.01,4)
thresh <- 10.3
pctile <- 0.025 psooptim control, vectorized but still only uses 1 core
ctrl <- list(reltol=2e-01, abstol=5e-01, maxf=1e04, maxit=1e03, maxit.stagnate=1e02,
        vectorize=TRUE, c.p=1.8, c.g=1.8, w=c(0.7,0.9), s=50, p=0.8,
        hybrid=TRUE, hybrid.control=list(maxit=1e03), trace=1, REPORT=1000)
# dsm$par is vector of epsilon adjustments
dsm$value = 0 is minimized value of hankel.obj when fnscale=1 alternate control
ctrl <- list(reltol=2e-01, abstol=5e-01, maxf=1e04, maxit=1e03, maxit.stagnate=1e02,
        vectorize=TRUE, c.p=1.2, c.g=1.2, w=c(0.5,0.5), s=30, p=0.5,
        hybrid=TRUE, hybrid.control=list(maxit=1e03), trace=0, REPORT=1000)

# EWMA smoothing
lambda <- 0.7
# inline slightly faster than recursion
ewma4 <- function(s) {
    p <- lambda*s[1,2] + (1 - lambda)*s[1,1]
    q <- lambda*s[1,3] + (1 - lambda)*p
    r <- lambda*s[2,3] + (1 - lambda)*q
    return(r)
} hankel matrix examples to solve with y[3,3] non-NULL dummy value, preferably EWMA estimate
may need to add small amount of noise to y to avoid det(x) = 0
# if solver converges, the forecast is value of y[3,3]
# lower and upper parms can be extrema of plausible values
# even if solver does not converge in maxit or maxf, the $par array does contain plausible estimates for y[3,3]
# iterate N times and take the range as plausible prediction interval for next value y5
                            .
                            .
                            .
```

*FIG. 4B*

CONTINUES FROM FIG. 4B

.
.
.

```
# function to transform time series 4-vector to matrix for Hankel difference equation model
vec4.trans <- function(v){
  if (length(v) != 4) stop("wrong time series length")
  tmp <- matrix(rep(0,9), ncol=3)
  tmp[1,1:3] <- v[1:3]
  tmp[2,1:3] <- v[2:4]
  tmp[3,1:2] <- v[3:4]
  y <<- tmp
} function to calculate 5th percentile of next eGFR result from 1000 trials of Particle Swarm
Optimization forecasting of difference equation from 4 previous eGFR values
psonext <- function(v){
  y5 <- rep(NA, 2000)
  y <- vec4.trans(v)
  y[3,3] <- ewma4(y)
  ul <- mean(y) + 4*sd(y)
  ll <- mean(y) - 4*sd(y)
  for (i in 1:2000) {
    set.seed(as.numeric(Sys.time()))
    dsm <- psoptim(e, hankel.obj.pso, lower=ll, upper=ul, control=ctrl)
    if(dsm$convergence > 0 || y[3,3] < 0)
      {
        y5[i] <- median(dsm$par)
      }else{
        y5[i] <- y[3,3]
      }
  }
  quantile(y5,pctile) < thresh
}

#---------------------------
# true-positive <8.9>
egfr <- c(16.9,12.3,10.8,9.7)
psonext(egfr)

#---------------------------
# true-positive <8.4>
egfr <- c(11.3,12.1,9.6,8.2)
psonext(egfr)

#---------------------------
# true-negative <10.9>
egfr <- c(10.3,12.1,10.4,10.8)
psonext(egfr)

#---------------------------
# true-negative <11.8>
egfr <- c(15.3,12.3,12.0,11.9)
psonext(egfr)
```

*FIG. 4C*

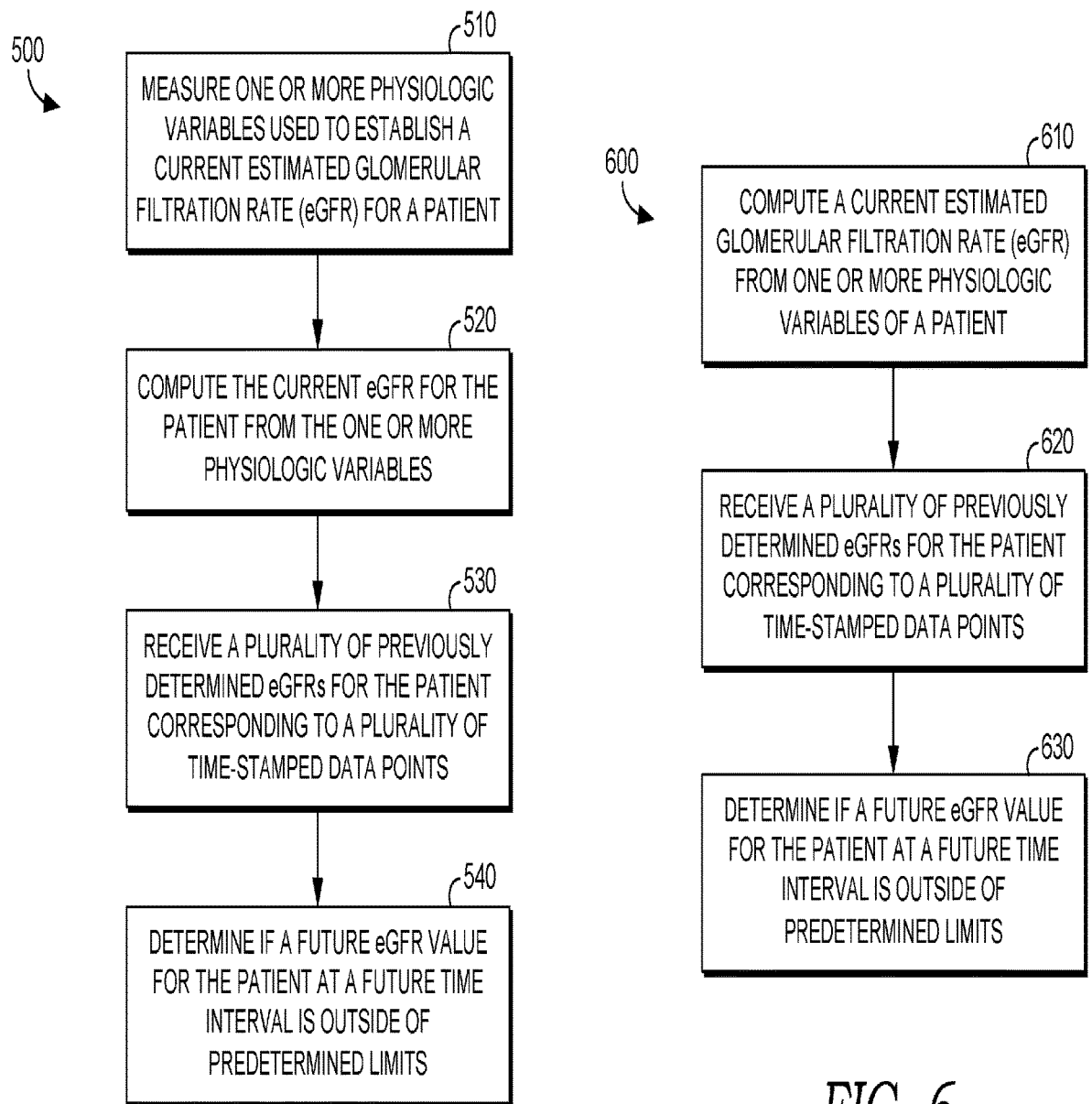

COMPUTER DECISION SUPPORT FOR DETERMINING SURGERY CANDIDACY IN STAGE FOUR CHRONIC KIDNEY DISEASE

CROSS-REFERENCE TO RELATED APPLICATIONS

This application claims the benefit of U.S. Non-Provisional application Ser. No. 15/144,378, titled "COMPUTER DECISION SUPPORT FOR DETERMINING SURGERY CANDIDACY IN STAGE FOUR CHRONIC KIDNEY DISEASE," filed on Monday, May 2, 2016, which claims the benefit of U.S. Provisional Application No. 62/155,629, titled "DETERMINING SURGERY CANDIDACY IN STAGE FOUR CHRONIC KIDNEY DISEASE," filed on May 1, 2015; both of which are hereby expressly incorporated by reference in its entirety.

BACKGROUND

Chronic kidney disease (CKD) is one of the major health concerns facing the developed world. In the U.S. alone, 26 million people have CKD and another 20 million more are at increased risk. CKD leads to dialysis and heart disease. In 2012, total Medicare expenditures for all stages of kidney disease was over $87 billion (not including prescription medications). The majority of these expenses, about $58B, were spent caring for those with CKD, including dialysis services. More than 615,000 Americans are being treated for kidney failure, also called end stage renal disease, or ESRD. Of these, more than 430,000 are dialysis patients and more than 185,000 have a functioning kidney transplant. There are approximately 5,938 dialysis facilities in the U.S. Of these dialysis facilities, approximately 765 are hospital-based.

In many cases, deterioration of kidney function in CKD occurs in a relatively orderly pattern of progression, albeit often with intermittent bouts of acute exacerbation followed by partial remission for a period of months. However, a present difficulty is that many persons with CKD experience progression that is relatively disorderly or chaotic, resulting in their precipitously transitioning from CKD Stage 4 to Stage 5 and end-stage renal disease (ESRD) with inadequate time to arrange for surgical placement of vascular access (arteriovenous fistula (AVF), arteriovenous graft (AVG), etc.) to support hemodialysis.

SUMMARY

Systems, methods and computer-readable media are provided for predicting candidacy for Kidney Surgery. In particular, embodiments of the disclosure are directed to computer-performed decision support technology for identifying populations of patients who are candidates for vascular access placement in CKD. Some embodiments of the present disclosure provide a computerized system and method for continually tracking the clinical and physiologic status of a patient in a hospital. At least some of the embodiments assist nephrologists in preventing and reducing the frequency of crises in urgent/emergent presentation with requirement for dialysis ("crashing onto dialysis") by using the systems' capability to recognize patterns in a patient's estimated glomerular filtration rate (eGFR) and serum uric acid values before the patient deteriorates or reaches a crisis.

Moreover, recognizing a high risk of deterioration far enough in advance of the onset of deterioration can allow a rational allocation of resources, including intensified monitoring or treatments that may reduce the risk of an urgent/emergent requirement for dialysis arising from chaotic progression of chronic kidney disease or other health conditions. Additionally, a timelier placement of vascular access may enable (a) a reduction in short-term mortality for patients whose initiation of dialysis is planned and not emergent, (b) improved fistula or graft maturation, with improvement of vascular access patency and usability secondary to this, and (c) a decreased length-of-stay in acute care institutions, with corresponding financial savings, as well as other benefits. Accordingly, some embodiments comprise computer-performed method for providing decision support such as by detecting likelihood of patient deterioration before conventional patient monitors would otherwise detect patient risk, and further by determining and providing patient treatment recommendations, alerting caregivers, automatically scheduling healthcare resources, or generating, modifying, or invoking healthcare computer programs to facilitate treatment and management of the patient.

Further, some embodiments of the present disclosure generate near-term forecasts which may be periodically plotted and displayed to show each patient's risk trend during his/her management by nephrologists and other clinicians. Some embodiments may include an interface module for receiving incoming medical data from a patient, a transformation module for transforming the medical data into a forecasted value, and a combination module for combining successive forecasts into single value, which may be utilized for providing compute-performed decision support.

BRIEF DESCRIPTION OF THE DRAWINGS

The present technology is described in detail below with reference to the attached drawing figures, which are intended to be exemplary and non-limiting in nature, wherein:

FIGS. 4A-4C provide an exemplary computer program routine used for implementing an embodiment of the disclosure;

FIG. 5 is a block diagram of an exemplary method for predicting candidacy for vascular access placement in a patient suffering from chronic kidney disease, in accordance with an embodiment of the present disclosure; and FIG. 6 is a block diagram of an exemplary method for predicting candidacy for vascular access placement in a patient in stage four chronic kidney disease, in accordance with an embodiment of the present disclosure.

DETAILED DESCRIPTION

Figure 1A:
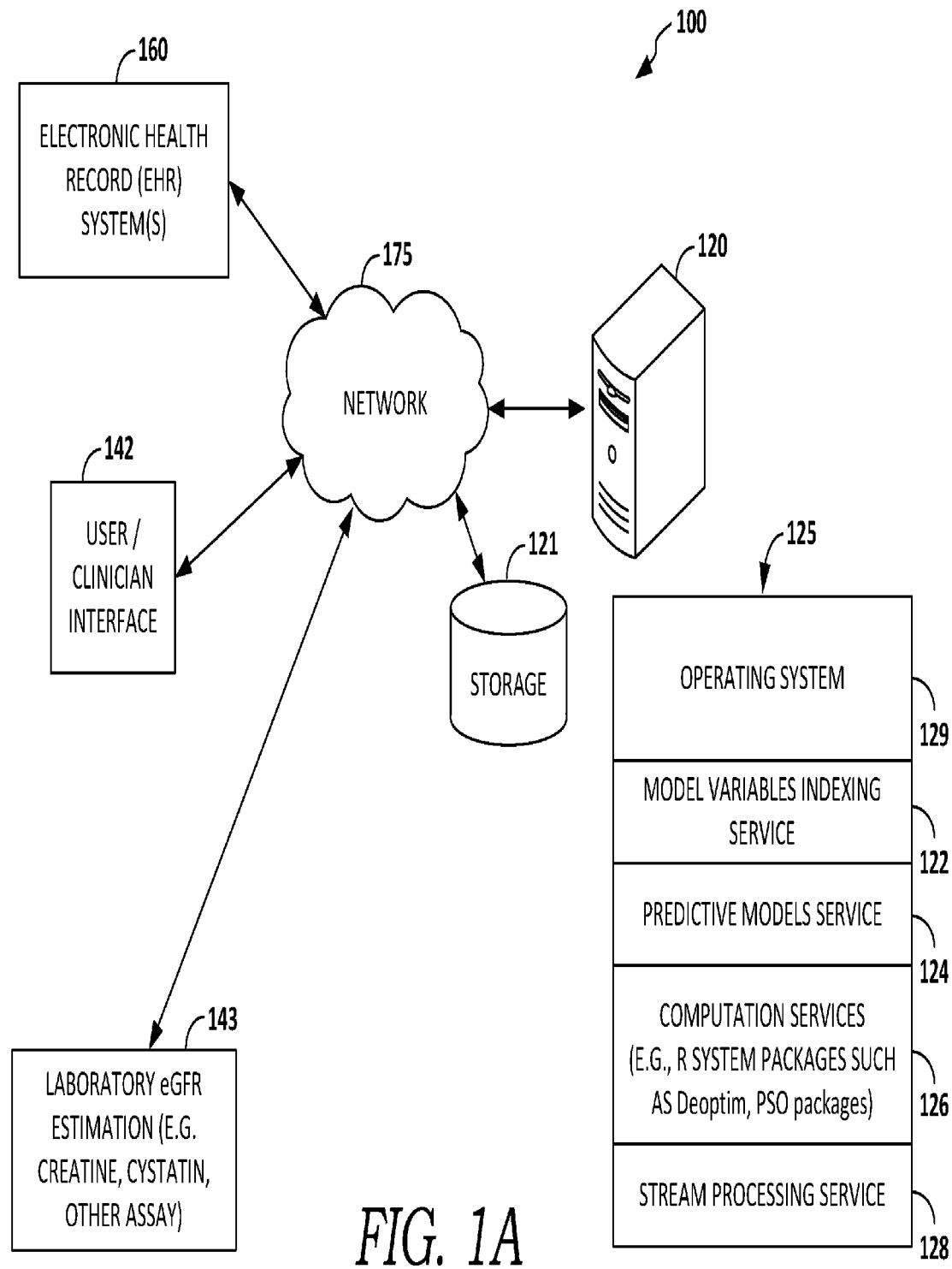
FIGS. 1A and 1B depict aspects of an illustrative operating environment suitable for practicing an embodiment of the present disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things, a method, a system, or a set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules, or other data.

Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer-readable media.

Accordingly, at a high level, this disclosure describes, among other things, methods and systems for identifying and monitoring patients who are candidates for vascular access placement in CKD and providing related computer-performed decision support services. Embodiments of the invention relate to predicting the likelihood of developing a need for dialysis within a future time interval, particularly in patients having CKD. More particularly, embodiments relate to predicting the need for dialysis and/or a time until a need for dialysis for the purpose of identifying candidates for surgical placement of vascular access, such as an arteriovenous fistula or graft, at a time sufficiently far in advance of the predicted likely need for dialysis so that the surgical procedure can be completed. This may provide access tissues sufficient time to heal and mature so as to be able to support cannulation for hemodialysis at the time when dialysis becomes necessary. Embodiments of the invention may also provide risk stratification by identifying patients that will require enhanced monitoring, and/or that will benefit most from initiating early intensification of therapy.

Dialysis is a type of renal replacement therapy that provides a substitute for kidney function that has been lost. It is primarily a life support treatment and usually does not cure any kidney diseases. Dialysis may be used for very sick patients who have suddenly lost their kidney function (e.g., acute renal failure (ARF); acute kidney injury (AKI), or for patients whose kidney function is progressively deteriorating (chronic renal failure (CRF); chronic kidney disease (CKD)) until initiation of dialysis becomes necessary to treat uremia (end stage renal disease (ESRD)).

It is possible to live with chronically decreased kidney function. Only when the amount of functioning kidney tissue is markedly diminished will clinically significant uremia develop. Such decompensation of kidney function may affect the function of many other organs and naturally lead to death due to uremia. In acutely or chronically decompensated patients with severe uremia, immediate renal replacement therapy is indicated, either by dialysis or renal transplantation. However, in contrast to the usually observed chronic deterioration and progressive decompensation of kidney function, renal failure may occur suddenly and unexpectedly even in patients previously considered to have stable kidney function. Such sudden deteriorations may be caused by infections, shock or hemodynamics abnormalities, or toxic side-effects of various medical therapies. Although established laboratory values to estimate the degree of renal dysfunction exist (see below), it would be highly desirable to have easy prognostic means and methods, such as a biomarker, to identify patients at risk of developing a need for dialysis.

Most practitioners use the plasma concentrations of creatinine, urea, cystatin C, and electrolytes to determine renal function. These measures are adequate to determine whether a patient is suffering from kidney disease. Unfortunately, blood urea nitrogen and creatinine are often not outside of a normal range until 60% of total kidney function has been lost.

In renal patients, estimates of the glomerular filtration rate (GFR) are used to assess kidney function. The GFR is classically calculated by comparing urine creatinine levels with blood test results. It gives a more precise indication of the state of the kidneys' ability to filter various solutes from the bloodstream. However, more convenient means of estimating the GFR have long been known. Such methods calculate estimated GFR (eGFR) using only serum creatinine measurement, plus patient age, weight, height, race, or other variables. GFR and eGFR values are expressed in ml/min/1.73 m2 (milliliters per minute per 1.73 square meters of body surface area). For most patients, a GFR over 60 mL/min/1.73 m2 is adequate. But, if the GFR has significantly declined from a previous test result, this can be an indicator of kidney disease progression requiring medical intervention.

In addition to the foregoing, an elevated serum level of uric acid (hyperuricemia) is known to be associated with an accelerated decline in eGFR and a higher risk of CKD progression. Conversely, hypouricemia has also been linked to reduced renal function, and evidence indicates that it may be associated with acceleration of the decline in GFR and progression of chronic kidney disease (CKD), possibly by way of a mechanism involving excessive filtration (such CKD patients are termed "hyper-filtrators").

Accordingly, a method for predicting the risk and time frame for developing a need for dialysis in a patient with chronic renal failure is provided, in accordance with an embodiment of the present disclosure. The method comprises (a) determining, for the patient, a level of uric acid in a serum sample taken from the patient, (b) determining serial serum creatinine or cystatin C values from the measured level of uric acid, and in some embodiments, combining this with age, gender, height, weight, racial or ethnic group, and other optional variables, (c) calculating serial eGFR values (which in some embodiments, are separated by time intervals of at least 2 weeks), (d) estimating a rate of change with time (which may be determined as a slope) from at least 3 such serial eGFR values, (e) combining the eGFR slope value and the uric acid value to estimate a likelihood of the patient progressing to a requirement for dialysis within a future time interval, such as 180 days from the present date, (f) calculating the likely next future value of eGFR using an evolutionary algorithm, such as particle swarm optimization or differential evolution, and (g) combining the values from (d) and (e) to determine a composite prediction of the likelihood of the patient requiring dialysis within a future time interval.

Additional embodiments may allow a particularly early diagnosis of the risk (and/or prediction) of a patient developing a need for dialysis. Consequently, patients at increased risk of near-term serious decompensation of kidney function may also be identified. Thus, it is possible to adjust and optimize renoprotective therapy earlier than would routinely be the case for the patient. Accordingly, a personalized treatment plan for a patient who is identified as having an increased risk for the need of dialysis may be provided.

Furthermore, in this manner, arranging for a suitable accompanying treatment or monitoring with respect to a determined risk may also be provided. Consequently, methods for risk stratification, particularly with respect to patients who will require closer monitoring and/or benefit most from initiating early intensified treatment by nephrologists, may be provided.

CKD can be diagnosed by any means known and deemed appropriate. Particularly, renal function can be assessed by analyzing a patient's eGFR. For example, the eGFR may be calculated by the Cockgroft-Gault or the MDRD formula [Levey 1999]. GFR is the volume of fluid filtered from the renal glomerular capillaries into the Bowman's capsule per unit time. Clinically, this is routinely used to determine renal function. The GFR is typically recorded in milliliters per minute (mL/min/1.73 m2), where the ratio is normalized to a standardized patient body surface area of 1.73 m2.

If the eGFR has decreased below a critical threshold which allows removal of toxic concentration of urea from the blood (usually at an eGFR or creatinine clearance <15 mL/min/1.73 m2 corresponding to end-stage renal disease), then, depending upon other clinical circumstances, such as the patients clinical condition, renal replacement therapy is indicated. A GFR of less than 10 mL/min/1.73 m2 preferably indicates an impending need for dialysis and a GFR of less than 6 mL/min/1.73 m2 preferably indicates an immediate need for dialysis. Dialysis is also preferably indicated if the patient has a GFR of less than 15 mL/min/1.73 m2 and exhibits at least one of the following clinical conditions: symptoms or signs of uremia, diuretic resistant fluid overload, poorly controlled blood pressure, and evidence of malnutrition.

It is to be understood as set forth elsewhere in this disclosure that the risk stratification provided by the method of the present disclosure preferably relates to a defined time window ('predictive window') in the future. The predictive window is an interval of time in which the subject may likely develop the need for dialysis according to the predicted probability. Preferably, the predictive window is an interval of several months or up to one year after the most recent serum sample is taken for analysis by some embodiments of the present disclosure.

A significant limitation of conventional approaches is limited statistical sensitivity and specificity, with substantial false-negative and false-positive rates. Most of the prior art regression equations, CART, decision-tree, neural-network, and other classification algorithms are only able to achieve Receiver Operating Characteristic (ROC) area-under-the-curve (AUC) discrimination performance of lower than 75%.

Another limitation of conventional approaches is that variables included in the predictions are often, at least temporally, "lagging indicators" (e.g., albuminuria, or other metabolic indicators of kidney function), which broadly characterize a background of diminished organ-system capacity related to filtration and clearance of solutes from the blood.

The present technology also provides a system and method for calculating and communicating a numerical probability of an event in patients, and especially patients in whom other scores yield excessive false-negative results. Despite the superior sensitivity to accurately recognize patients at-risk whose abnormalities are not obvious, the present technology simultaneously achieves specificity that is superior to the prior art. The ROC AUC of the present technology is approximately 89% in the populations examined to-date. In part, this greater accuracy and discriminatory power to classify individual cases correctly is due to the utilization of evolutionary time series analytical methods, especially particle-swarm optimization (PSO) and differential evolution (DE) algorithms, which enable inferences based on a short time-series consisting of a small plurality of observational time points (e.g., data from as few as 4 serial measurements).

In one embodiment, an evolutionary analysis that estimates a statistical forecast for a next epoch immediately beyond the present one is provided. There are some deterioration events that are acute, with sudden onset and no apparent antecedent abnormality or multivariate cluster of abnormalities that predict the imminent event. Fortunately, from the screening and diagnostic perspective, a majority of patients who deteriorate have a prodrome of renal function abnormalities for weeks or months in advance of the onset of deterioration. This may afford a "window of opportunity" sufficient for undertaking effective preventive and corrective actions, as well as intensified monitoring, to allow intervention to occur more quickly and effectively.

In many instances, the prodrome involves a change in statistical relationships (e.g., autocorrelation of one variable with itself, cross-correlations between pairs of variables, etc.) that bear on the natural physiologic coupling between the organ systems and processes that give rise to the measured variables. For example, the relation of eGFR to uric acid and other surrogate measures of oxidative metabolism may be identified as the prodrome. The statistical distributions of the values taken on by the terms in derived, composite variables are both skewed and asymmetric. This is true both under normal conditions and under various pathophysiologic conditions that give rise to actionable events that relate to medical outcomes.

The practical reality, however, is that statistical tests of the goodness-of-fit of distributions of data require a considerable number of observations in order to produce a reliable conclusion or p-value. In the present disclosure, the model development dataset and model validation dataset can generate stable, reliable p-values for PSO or DE forecasts based on as little as 4 prior measurements, either of the eGFR by itself or of derived variables such as eGFR slope or eGFR*uric_acid.

Some embodiments of the technology avoid most of the limitations of the prior art and achieve superior predictive accuracy and statistical discrimination compared to other scores. This occurs (a) by analyzing physiologic time series as arising from an "algebraic evolution" and (b) by processing the resulting array of information so as to generate a predicted value for the time series at one or more future time points.

In context of embodiments of the disclosure described herein, the term "progression of chronic kidney disease" or "chronic kidney disease progression" may mean, for example, a doubling of baseline serum (or plasma) creatinine concentration and/or terminal real failure necessitating renal replacement therapy, such as dialysis (e.g., hemodialysis, peritoneal dialysis, etc.) or even renal transplantation. The definition of the "progression of chronic kidney disease" is very well known in the art. Accordingly, the "progression of chronic kidney disease" can be determined, in a primary endpoint, as the doubling of the base-line serum creatinine or the need for dialysis or kidney transplantation. However, those experienced in the art appreciate that predicting the progression of CKD is difficult.

The Kidney Disease Improving Global Outcomes (KDIGO) guidelines define and stage acute and chronic kidney diseases by GFR. For initial assessment of GFR, measuring serum creatinine and reporting eGFR based on serum creatinine (eGFRcr) using the Chronic Kidney Disease Epidemiology Collaboration (CKD-EPI) equation is recommended. If confirmation of GFR is required because of conditions that affect serum creatinine independent of GFR (e.g., cachexia or diet changes), or interference with the assay, cystatin C should be measured and eGFR should be calculated and reported using cystatin C (eGFRcys) and serum creatinine (eGFRcr-cys), or GFR should be measured directly using a clearance procedure.

Renal hyperfiltration has been described to occur in renal and non-renal clinical conditions. The definition of glomerular hyperfiltration has not been agreed upon and the pathophysiological mechanisms have not been well explored. However, an eGFR of 125 to 140 mL/min/1.73 $m^2$, or >2 SD above mean eGFR in healthy individuals is a commonly accepted definition. In humans, renal hyperfiltration observed in early diabetes mellitus is a risk factor for the development of diabetic nephropathy. More recently, renal hyperfiltration has been reported in obesity and metabolic syndrome and in pre-diabetic subjects with impaired fasting glucose. The pathogenesis of hyperfiltration is incompletely understood and attributed to glomerular afferent and efferent arteriolar tone as well as to renal tubule physiology. Others have proposed a tubulo-glomerular feedback hypothesis.

The CKD-EPI equation for eGFR truncates serum creatinine values below 0.9 mg/dL, which causes the eGFR values to be artifactually high. By contrast, the MDRD equation for eGFR does not truncate low creatinine values and has the advantage of disclosing absolute "hyperfiltrators," as noted in eGFR quartiles [Altay 2014; Matsushita 2012]. The MDRD equation has certain advantages with regard to prognostic accuracy in individuals with CKD. The superiority of the CKD-EPI equation is accepted in epidemiological studies, but it does have superiority in N-of-1 decision-making for an individual patient. For longitudinally monitoring the GFR of a given individual, the precision of the estimate has dominant importance and, in this context, the CKD-EPI equation lacks any advantage.

Aging is associated with structural and functional changes in the kidney. Structural changes include glomerulosclerosis, thickening of the basement membrane, increase in mesangial matrix, tubulointerstitial fibrosis, and arteriosclerosis [Wiggins 2011]. Glomerular filtration rate is maintained until the fourth decade of life, after which it declines. Parallel reductions in renal blood flow occur with redistribution of blood flow from the cortex to the medulla. Other functional changes include an increase in glomerular basement membrane permeability and decreased ability to dilute or concentrate urine. Functional reserve and compensatory renal capacity wane with increasing age.

The recent trend toward "early" initiation of dialysis at eGFR >10 mL/min/1.73 m2 is now widely regarded as having been based on subjective wisdoms that are not supported by objective evidence. Observational studies using administrative databases report worse comorbidity-adjusted dialysis survival with early dialysis initiation. Although some have concluded that the IDEAL randomized controlled trial of dialysis start provided evidence that patients become symptomatic with late dialysis start, there is no definitive support for this view. The potential harms of early start of dialysis, including the loss of residual renal function (RRF), have been well documented. The rate of RRF loss (renal function trajectory) is an important consideration for the timing of the dialysis initiation decision. Patients with low glomerular filtration rate (GFR) may have sufficient RRF to be maintained off dialysis for years. Delay of dialysis start until an adequately-matured, healed arteriovenous access is in place seems prudent in light of the absence of harm (and possible benefit) of "late" dialysis initiation. Preemptive start of dialysis in non-compliant patients may be necessary to optimize outcomes and minimize complications. However, there is presently no data to show that "early" start of dialysis benefits diabetics or other patient groups.

Some embodiments of the present technology predict the likelihood of near-term deterioration to eGFR between 6 and 10 mL/min/1.73 m2, both in the case of patients whose CKD progression is orderly and in the case of patients whose CKD progression is comparatively chaotic and marked by intermittent exacerbations and partial remissions (having wide fluctuations in serial eGFR values). In the present application, evolutionary algorithms, such as particle swarm optimization or differential evolution, are a novel means of establishing such predictions in the latter group.

When an objective function's minimum is non-stationary, its moving average location drifts and the optimization goal is one of tracking the optimal vector on short sequences of observations, on short time-scales, or both. In the case of acute-care monitoring where the status of the patient often changes relatively quickly, the optimum may drift rapidly. Further, the systems that give rise to the measured data tend to embody a chaotic, stochastic process for which a least-mean-square, or a recursive least-square deterministic optimizer that requires estimating a derivative with respect to time, does not produce forecasts of adequate accuracy.

Some embodiments of the present disclosure entail a system and method that can accommodate rapid-drift non-differentiable processes by initializing algebraic evolution solvers staggered in time. These solvers operate in parallel, and each successively converges and returns its result to another solver that combines a plurality of the serialized results into a combined ensemble forecast for the value that will be measured at the next observation. Some embodiments do not require that the serial measurements be made at precise, periodic intervals but instead tolerates significant clock or phase jitter in the measured time series.

In this way, embodiments of the present technology overcome certain drawbacks associated with the prior art by providing a means for longitudinally calculating and tracking the patient's risk of acute deterioration while in a hospital. Systems and methods for providing a predicted probability of acute deterioration for a hospitalized patient are also disclosed herein.

According to some aspects of the present technology illustrated herein, there is provided a computer-performed decision support system, which may comprise generating an indicator of a patient's probability of acute deterioration, the system including a data module receiving data relating to a patient's vital signs, and a data transformation and statistical computation module generating an output from the data, the output representing the patient's likelihood of deteriorating acutely. In some embodiments, the system further comprises one or more of notification module for providing an alert or notification, a communication module for communicating the alert, a display module for displaying the output, and a scheduling module for scheduling healthcare resources for treating or managing the patient.

In the context of the present disclosure, DE, PSO, and other similar evolutionary algorithms as are known to those practiced in the art may be used. Each appears to possess strengths and limitations with respect to particular applications in renal function variables forecasting. Regardless of which of the algorithms described below is employed to provide an optimization, the algebraic evolution formalism utilizing Hankel matrices and objective functions of the type disclosed herein is a principal source of the novelty and non-obviousness of the present technology.

Particle swarm optimization (PSO) is an algorithm that performs population-based stochastic search and optimization. PSO originated from computer simulation of individual "particles," such as members of a flock of migratory birds flying or a school of fish swimming Swarms consisting of many individuals establish an overall direction of movement collectively and socially, in a self-organizing manner that responds to optimum directions initially undertaken by one or a few individual members. Each particle keeps track of its own position in the search space and its own best solution so far achieved. The PSO process also keeps track of the globally best solution achieved by the swarm.

During the exploration across the search space with discrete-time iterations, the velocity of each PSO agent is computed as a function of the best position of the swarm, the best personal position of each particle, and its previous velocity. These components contribute randomly to the position of each particle in the next iteration or generation of the swarm. Together, the generations exhibit a tendency toward survival of the fittest and global best in terms of minimizing the objective function. The probability of success is increased due to the large number of particles in the swarm, since success requires merely that one member of the swarm succeed. As such, PSO is able to efficiently discover correct global optima even when presented with optimization search spaces that have many local minima and nonlinearities or discontinuities.

Differential evolution (DE) is an evolutionary algorithm that has similarities to so-called genetic algorithms (GA). DE has certain differences insofar as it is applicable to real-valued vectors rather than bit-encoded strings. Accordingly, the DE algorithm's mutation and cross-over operations are different from those in GA. Notably, the mutation operator is different in its way of becoming trapped in local minima of the function being optimized. Like PSO, DE has population members or agents that effectively sample the search space of possible function values. For each successive generation of agents, mutation and cross-over operators are applied to each agent's vector, a numerical objective function fitness is calculated, and the best of that generation's members are propagated to the next generation and the process is repeated until the fitness converges to an asymptotic value. If any agent achieves the objective fitness score or the maximum number of generations set as a limit, then the process is terminated. PSO and DE have been utilized to numerically solve other equations relating to phenomena in nonlinear wave motion, soliton physics, Kortweg-de Vries equations, Kadomtsev-Petviashvili equations, and the nonlinear Schrödinger equation.

Referring now to the drawings in general, and initially to FIG. 1A, an operating environment 100 is provided that is suitable for practicing an embodiment of the present technology. Certain items in block-diagram form are provided to allow for consistent reference, and are not intended to imply that a certain component is or is not part of a certain device. Similarly, although some items are depicted in the singular form, plural items are contemplated as well (e.g., what is shown as one data store might really be multiple data-stores, possibly distributed across multiple locations). Because showing every variation of each item might obscure the disclosure, for readability, the reference items are shown in the singular (while fully contemplating, where applicable, the plural).

As shown in FIG. 1, the operating environment 100 provides an aspect of a computerized system for compiling and/or running aspects of the present technology including collecting and analyzing unstructured text data from electronic health record(s) (EHRs) to assess the texts as to topical or concept-oriented expressions they contain that are statistically similar to those associated with various clinical conditions or diagnoses, to identify which condition(s) or diagnosis-oriented cluster(s) the present texts most closely resemble, if any, and to notify the responsible clinicians of those determinations, suggesting consideration of those conditions or diagnoses as part of the constellation of differential diagnoses pertinent to the management of the current patient.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system 160 may perform functions for two or more of the EHR systems (not shown).

Network 175 may comprise the Internet, and/or one or more public networks, private networks, or other communications networks such as a cellular network or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors, for example. Although FIG. 1A depicts an exemplary EHR system 160, it is contemplated that an embodiment relies on user laboratory eGPR estimation component 143 for determining patient lab-related record information.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 may take the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet.

A provider clinician application facilitates accessing and receiving information from a user or health care provider about a specific patient or set of patients for which the likelihood(s) of future events such as acute risk of deterioration are determined according to the embodiments presented herein. Embodiments of interface 142 also facilitates accessing and receiving information from a user or health care provider about a specific patient or population of patients including patient history, healthcare resource data, variables, measurements, time series, and predictions (including plotting or displaying the determined outcome and/or issuing an alert) described herein, or other health-related information. Interface 142 may also facilitate the display of results, recommendations, or orders, for example. In an embodiment, the interface 142 also facilitates receiving orders for the patient from the clinician/user, based on the results of monitoring and predictions. Interface 142 may also be used for providing diagnostic services or evaluation of the performance of various embodiments. As shown in example environment 100, in one embodiment, laboratory eGPR estimation component 143 is connected to network 175. In an embodiment, laboratory eGPR estimation component 143 communicates via network 175 to computer 120 and/or provider clinician interface 142.

An embodiment of laboratory eGPR estimation component 143 (sometimes referred to herein as a patient-interface component) comprises one or more sensor components operable to acquire clinical or physiological information about a patient, as described herein. In one embodiment, component 143 comprises sensors for obtaining and analyzing the serial measurements of physiological data. In some embodiments, component 143 comprises a patient bedside monitor, such as those used in hospitals. In an embodiment, one or more sensor components of component 143 may comprise a user-wearable sensor component or sensor component integrated into the patient's environment. Examples of sensor components used with component 143 include a sensor positioned on an appendage (on or near the user's head, attached to the user's clothing, worn around the user's head, neck, leg, arm, wrist, ankle, finger, etc.), a skin-patch sensor; an ingestible or sub-dermal sensor; sensor component(s) integrated into the user's living environment (e.g., bed, pillow, or bathroom), and sensors operable with or through a smartphone carried by the user, for example.

It is also contemplated herein that clinical or physiological information about a patient, such as the monitored variables and/or clinical narratives regarding the patient, used according to the embodiment of the disclosure disclosed herein, may be received from human measurements, human observations, or automatically determined by sensors in proximity to the patient. For example, in one embodiment, a nurse periodically measures a patients' blood pressure and enters the measurement and/or observations via component 143 or interface 142. In another example, a nurse or caregiver enters one or more progress notes for an in-patient via manager 140 or interface 142. An embodiment of component 143 stores user-derived data locally or communicates data over network 175 to be stored remotely.

Example operating environment 100 further includes computer system 120, which may take the form of a server, which is communicatively coupled through network 175 to EHR system 160 and storage 121. Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud as a distributed system on a virtualization layer within computer system 120, and includes operating system 129. Operating system 129 may be implemented as a platform in the cloud, and may be capable of hosting a number of services such as a model variables indexing surface 122, a predictive models service 124, computation services 126 (e.g., R system packages such as AS Deoptim, PSO packages, etc.), and stream processing service 128. Some embodiments of operating system 129 may comprise a distributed adaptive agent operating system. Embodiments of services 122, 124, 126, and 128 may run as a local or distributed stack in the cloud, on one or more personal computers or servers such as system 120, and/or on a computing device running interfaces 140 and 142. In some embodiments, interface 142 operates in conjunction with software stack 125.

In embodiments, model variables indexing service 122 provides services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124 in general is responsible for providing multi-variable models for predicting candidacy for surgery, such as described in connection to method 200 of FIG. 2.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN; found at http://cran.r-project.org) or similar services. In an embodiment, computation services 126 include the services or routines, which may be embodied as one or more software agents or routines such as the example embodiments of computer program routines illustratively provided in FIGS. 4A-4C. In some embodiments, computation services 126 use EHR or lab information provided by a stream processing service 128.

Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more stream processing service(s) 128. For example, such stream processing service (s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the disclosure also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients). Storage 121 may include raw and/or processed patient data, variables associated with patient recommendations, a recommendation knowledge base, recommendation rules, recommendations, recommendation update statistics, an operational data store, which may store events, frequent itemsets (e.g., "X often happens with Y"), and item sets index information, association rulebases, agent libraries, solvers and solver libraries, and other similar information including data and computer-usable instructions, patient-derived data, and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
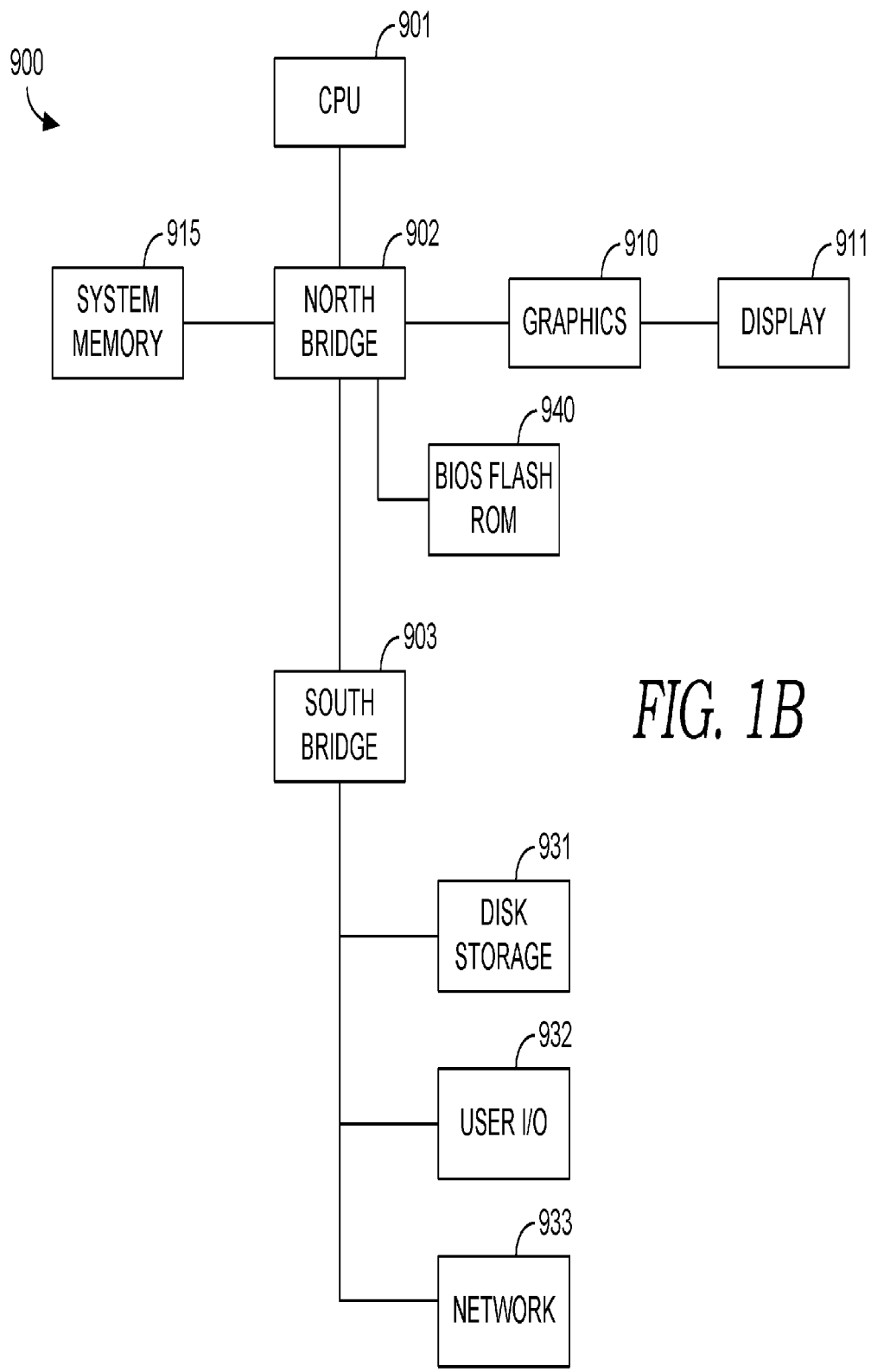

Turning briefly to FIG. 1B, provided is one example embodiment of computing system 900 that has software instructions for storage of data and programs embodied on computer-readable media. Computing system 900 is representative of a system architecture that is suitable for computer systems, such as computing system 120. One or more CPUs, such as CPU 901, have internal memory for storage, and are coupled to north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north bridge device 902 allowing CPU 901 to store instructions and data elements in disk storage 931, which may include a fixed disk or USB disk, or to make use of network 933 for remote storage. User I/O device 932, which may comprise a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
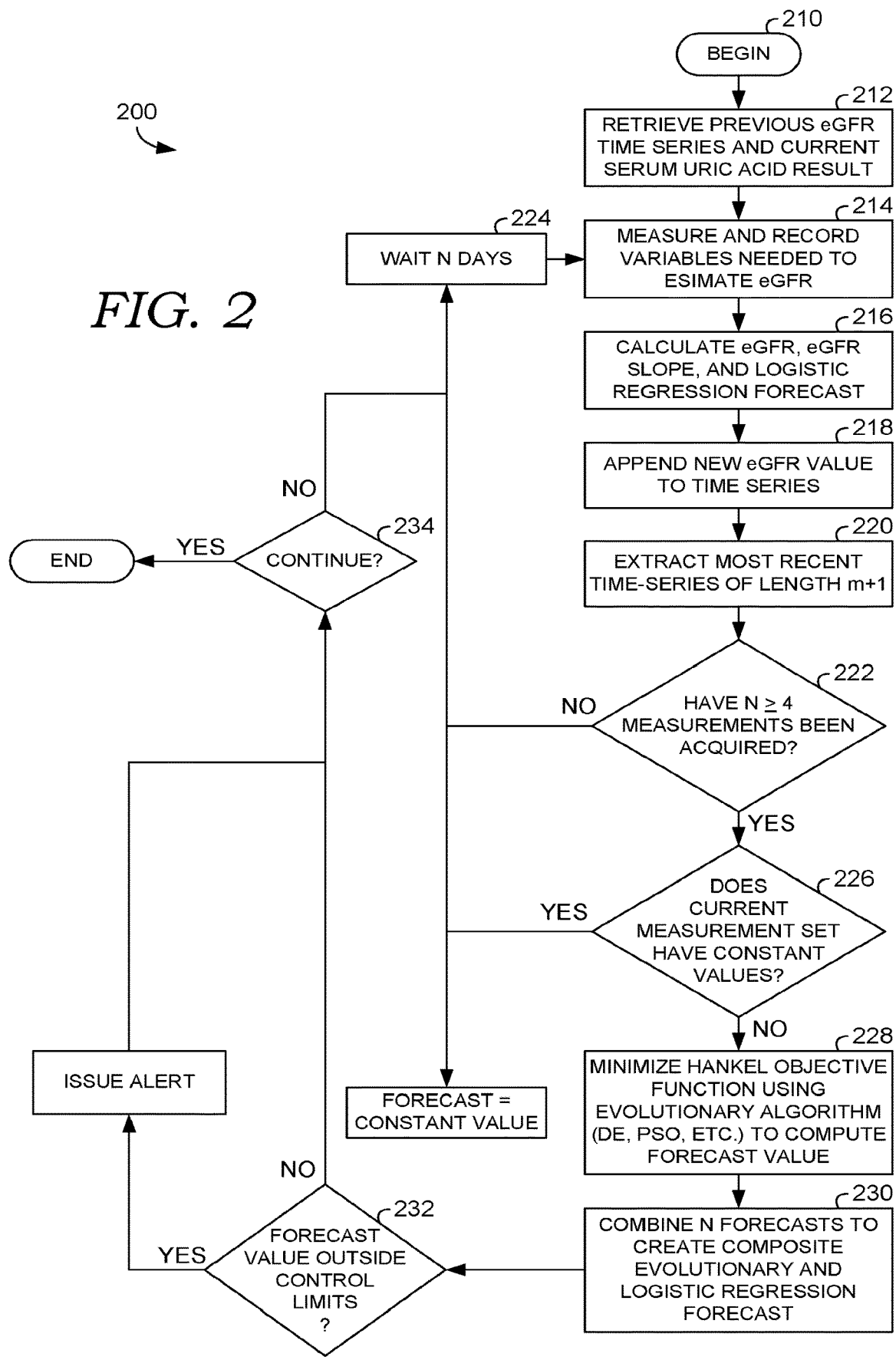
FIG. 2 depicts a flow diagram of a method of forecasting patient candidacy for vascular access placement in CKD, in accordance with an embodiment of the present disclosure.

Turning now to FIG. 2, an exemplary block diagram of a method 200 for forecasting populations of patients who are candidates for vascular access placement in Chronic Kidney Disease (CKD) is provided, in accordance with an embodiment of the present disclosure. In particular, method 200 comprises a process for acquiring the necessary data elements from a patient, the data flow for computing forecast values from these, and the logic and steps for combining successive forecasts into a composite to be communicated to appropriate clinicians who are responsible for the care of the patient. Such a composite of forecasts may be used to determine or predict, at a future time interval, when the patient may be a candidate for vascular access placement.

With reference generally to method 200 of FIG. 2 and also to FIGS. 4A-4C, time series forecasting is a challenge in many fields of science and engineering. Many approaches may be considered for time series forecasting. In general, the object of these approaches is to build a model of the process and then use this model on the last values of the time series to extrapolate past behavior into future behavior. Forecasting procedures may include different techniques and models, such as moving averages techniques, random walks and trend models, exponential smoothing, state space modeling, multivariate methods, vector autoregressive models, cointegrated and causal models, methods based on neural, fuzzy networks, or data mining, and rule-based techniques. These are typical methods used in time series forecasting.

The present technology involves a new method for the identification of an optimal set of time lags based on non-uniform attractor embedding from an observed non-linear time series. This may be used to provide a simple, deterministic method for the determination of non-uniform time lags that comprises the pre-processing stage of the time series forecasting algorithm.

A near-optimal set of time lags is identified by evolutionary algorithms, such as Particle Swarm Optimization (PSO) or Differential Evolution (DE). A solution fitness objective function is constructed in such a way that it represents the spreading of the attractor in the delay coordinate space but does not contain any information on prediction error metrics. A weighted one-point crossover rule enables an effective identification of near-optimal sets of non-uniform time lags which are better than the globally optimal set of uniform time lags. Thus, the reconstructed information on the properties of the underlying dynamical system is directly elaborated in the prediction system and method.

In forecasting physiologic variables, the concept of the rank of the Hankel matrix is exploited to detect a base algebraic fragment of the time series. PSO and other evolutionary algorithms are then used to remove the noise and identify the skeleton algebraic sequence that characterizes the time series and the underlying dynamical physiologic system that gives rise to the series.

The Hankel matrix H(m) is constructed from the elements of the time series sequence x={x0, x1, x2, . . . , xk}:

$$H^{(m)} = \begin{bmatrix} x_0 & x_1 & \ldots & x_{m-1} \\ x_1 & x_2 & \ldots & x_m \\ \vdots & & \ddots & \vdots \\ x_{m-1} & x_m & \ldots & x_{2m-2} \end{bmatrix} \quad \text{(Eq. 1)}$$

Determinants of Hankel matrices are denoted by det H(m). The rank of the sequence x is an integer m that satisfies the following conditions:

$$\det H^{(m+k)} = 0 \text{ and } \det H^{(m)} \neq 0, \text{ for all } k. \quad \text{(Eq. 2)}$$

If x is a completely chaotic, random sequence, then m=∞ (i.e., the sequence does not have a defined finite rank). However, if the sequence is not random and arises from an algebraic evolutionary process, then the following equality holds:

$$x_n = \sum_{k=1}^{r} \sum_{l=0}^{n_k-1} \mu_{kl}(l^n) \rho_k^{n-1}, \quad \text{(Eq. 3)}$$

where the characteristic roots ρk, k=1, 2, . . . , 4 can be determined from the Hankel characteristic equation:

$$\det \begin{bmatrix} x_0 & x_1 & \ldots & x_m \\ x_{m-1} & x_m & \ldots & x_{2m-1} \\ \vdots & & \ddots & \vdots \\ 1 & \rho & \ldots & \rho^m \end{bmatrix} \quad \text{(Eq. 4)}$$

where the coefficients μkl can be determined from a system of linear algebraic equations (3) for different values of n.

Due to the natural imprecision of measurement and various sources of noise in physiologic signals, the assumption that a sequence of such measurements is an algebraic evolution is, at best, an approximation. The forecasting of the next element x2n from (1) and (2) is not in general possible due to the inherent superimposed noise in real-world time series. Therefore, one embodiment proposes a set of adjustment or noise-compensating error terms εi, such that the next (seventh) element to be forecast in a 4-element time series represented by a 3×3 Hankel matrix is:

$$x[3, 3] = \frac{\begin{array}{l}(-(x[1,3]+e[3])*((x[1,2]+e[2])*(x[2,3]+\\ e[4])-(x[1,3]+e[3])^2)+((x[1,1]+e[1])*\\ (x[2,3]+e[4])*(x[1,3]+e[3]-(x[1,2]+e[2])))\end{array}}{(x[1,1]+e[1])*(x[1,3]+e[3])-(x[1,2]+e[2])^2} \quad \text{(Eq. 5)}$$

One embodiment sets forth an optimization fitness objective function to minimize, illustrated for the case of a sequence that is 4 elements in length:

$$F(x, \vec{e}) = \quad \text{(Eq. 6)}$$
$$\text{abs}\left[\det(x) * \left(0.25 * \sum_{1}^{4} \text{abs}(e_i) + \text{abs}(x[3,3] - EWMA(x))\right)\right]^{-1}$$

where EWMA is an exponentially-weighted moving average of the subset of the already-acquired elements in the sequence upon which the forecast is to be based.

The employment of evolutionary algorithms for the identification of the closest (smallest F(x,e)) algebraic skeleton sequences enables the system and method to achieve relatively high-quality predictions with sequences as short as 4 to 8 elements in length. The method is free of any assumptions regarding any statistical or physiologic dynamical properties of the measurements but instead performs local individual identification of the skeleton algebraic progression for every time step. The Mean Absolute Percentage Error (MAPE)

$$MAPE = \frac{100}{N} \sum_{1}^{N} |x_i - \hat{x}_i| \quad \text{(Eq. 7)}$$

for time series of length 4 is in the range 10% to 22% for the eGFR series to which the technology has been applied (see FIG. 3). As such, the forecast is sufficiently accurate to serve as an effective advisory aid to physicians wishing to ascertain the approximate risk that the patient's renal function will deteriorate (eGFR <10 mL/min/1.73 m2; requiring initiation of dialysis) within a time frame comparable to the frequency with which the successive eGFR measurements are being acquired. Conversely, the forecasts also appear to be sufficiently accurate to serve as an indication that therapeutic maneuvers that have already been undertaken are effective, adequate, and/or safe, and effective management of the CKD of the patient is occurring.

Figures 3A, 3B:
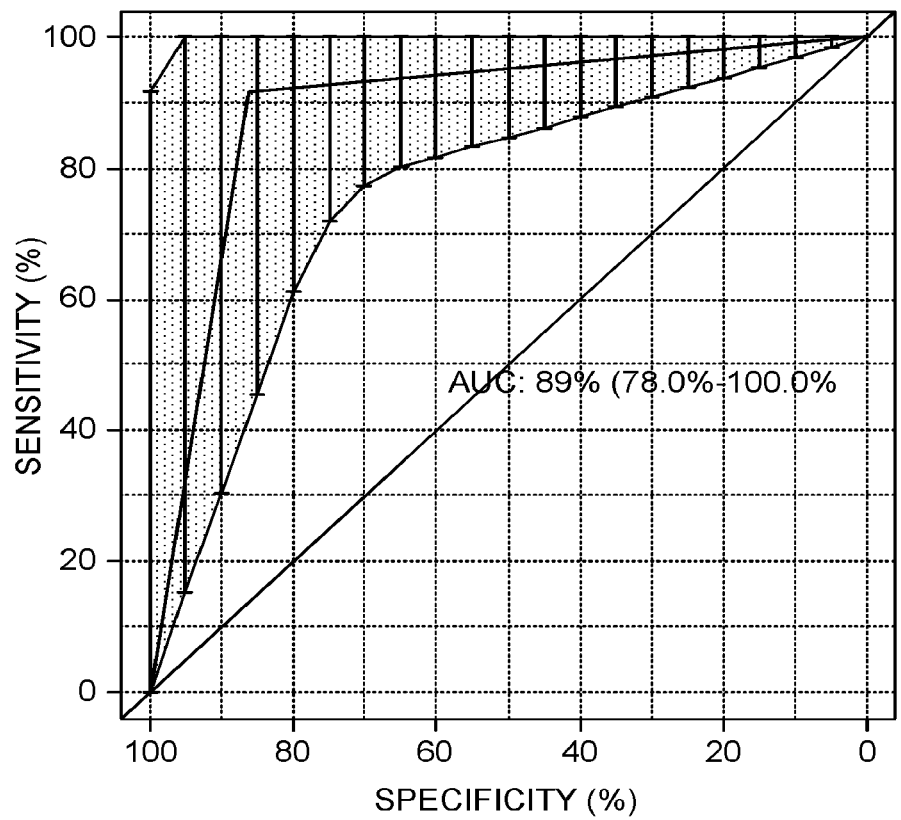
FIGS. 3A and 3B depict a Receiver Operating Characteristic (ROC) curve representing the accuracy of a forecasting system and method, and a table showing the statistical properties of the prognostic system and method in the population of CKD patients for whom an embodiment of the invention was reduced to practice, in accordance with an embodiment of the present disclosure.

For the testing and reduction-to-practice, a server cluster running the Linux operating system, the open-source statistical software package R, and the R module PSO may be used. A set of de-identified, secondary-use-consented, EHR-derived, HIPAA-compliant vital signs measurements from 35 human patients whose care episodes had previously been completed and for whom the initiation of dialysis outcomes were already known was extracted from a commercially-available datawarehouse (Cerner Health Facts®). eGFR time-series were computed for each of the 100 subjects and next-value forecasts were generated using PSO. The MAPE for the 4 time-point 90-day monitoring eGFR timeseries and prediction of requirement for dialysis at a date 180 days subsequent to the most recent eGFR and uric acid values was calculated for each, and the statistical sensitivity, specificity, and ROC area-under the curve (AUC) was computed (as shown in FIGS. 3A and 3B).

Referring back to FIG. 2, the exemplary method 200 is described in greater detail. At a block 210, a forecasting of whether a patient is a candidate for vascular access placement in CKD is initiated. At a block 212, a selection of previous eGFR values for the patient over a time series is obtained. In addition, a current serum uric acid result for the patient is collected and/or determined. At a block 214, a selection of variables needed to calculate a current eGFR value for the patient are measured (e.g., uric acid, serum creatinine, cystatin C values, etc.). At a block 216, the current eGFR value and the selection of previous eGFR values are used to determine a slope and compute a logistical regression forecast for the time series. At a block 218, the current eGFR value is appended to the time series. At a block 218, a most recent time series of length comprising m+1 is extracted from the time series. At a block 222, it is determined if at least four eGFR values over the time series of the length m+1 have been acquired.

If at least four eGFR values have not been acquired over the time series m+1, the process is delayed N days to allow further gathering of data, as shown in block 224. After N days, the recording of variables needed to estimate eGFR for a future time interval at block 214 are again initiated, and the process is repeated. If at least four eGFR values have been acquired over the most recent time series m+1, the current set of measured eGFR values is analyzed for constant values within predetermined control limits at block 226. If it is determined that the eGFR values are constant and within control limits, the forecast is determined to be that of a constant value, and the process returns to block 224 to wait N days until the measuring and recording of variables needed to estimate eGFR is again initiated at block 214.

If it is determined at block 226 that the current measurement set does not have constant values within predetermined control limits, the analysis proceeds to block 228. At block 228, a Hankel objective function is minimized using one or more evolutionary algorithms (e.g., differential evolution, particle swarm optimization, etc.) to compute a forecast value. At a block 230, a predetermined number of forecasts, such as N forecasts, are combined to create a composite evolutionary and logistic regression forecast. At a block 232, it is determined if the regression forecast is outside of the predetermined control limits. If the regression forecast is outside of the predetermined control limits, an alert may be issued, or another action may be taken for modification of care of the patient. At a block 234, if it is determined that the regression forecast is not outside of predetermined control limits, a selection to continue may be made.

With further reference to FIGS. 3A and 3B, a receiver operating characteristic (ROC) curve of the forecasting system and method set forth in an embodiment of the disclosure, as applied to the computation of forecasts for the shock index, is provided. As is known to those practiced in the art, the area under the ROC curve is a standard means of quantitatively assessing a classifier model's discrimination, or rather, the degree to which the model is able to accurately categorize cases into one or the other of two classes or categories—in this instance, "will deteriorate" to "will require hemodialysis within 180 days" (eGFR(180)<10 mL/min/1.73 m2) vs. "will not require hemodialysis within 180 days" (eGFR(180)<10 mL/min/1.73 m2). FIG. 3B shows a table of the statistical properties of the prognostic system and method in the population of CKD patients in whom an embodiment of the disclosure was reduced to practice and validated.

Turning to FIG. 5, a method 500 is depicted. At block 510, measure of one or more physiologic variables used to establish a current estimated glomerular filtration rate (eGFR) for a patient. At block 520, compute the current eGFR for the patient from the one or more physiologic variables. At block 530, receive a plurality of previously determined eGFR for the patient corresponding to a plurality of time-stamped data points. At block 540, determine if a future eGFR value for the patient at a future time interval is outside of predetermined limits.

Turning to FIG. 6, a method 600 is depicted. At block 610, compute a current estimated glomerular filtration rate (eGFR) from one or more physiologic variables of a patient. At block 620, receive a plurality of previously determined eGFRs for the patient corresponding to a plurality of time-stamped data points. At block 630, determine if a future eGFR value for the patient at a future time interval is outside of predetermined limits.

Embodiment 1: A method for predicting candidacy for vascular access placement in a patient suffering from chronic kidney disease, the method comprising measuring one or more physiologic variables used to establish a current estimated glomerular filtration rate (eGFR) for the patient; computing the current eGFR for the patient from the one or more physiologic variables; receiving a plurality of previously determined eGFRs for the patient corresponding to a plurality of time-stamped data points; and determining if a future eGFR value for the patient at a future time interval is outside of predetermined limits by determining an eGFR slope value from the current eGFR and the plurality of previously determined eGFRs, computing a first logistic regression forecast eGFR value using the current eGFR, the plurality of previously determined eGFRs, and the eGFR slope value, minimizing an objective function using one or more evolutionary algorithms to compute a second logistic regression forecast eGFR value using the current eGFR, the plurality of previously determined eGFRs, and the eGFR slope value, combining at least the first logistic regression forecast eGFR value and the second logistic regression forecast eGFR value to compute a composite regression forecast eGFR value, determining if at least one of the first logistic regression forecast eGFR value, the second logistic regression forecast eGFR value, and the composite regression forecast eGFR value is outside of the predetermined limits, and upon determining that at least one of the first logistic regression forecast eGFR value, the second logistic regression forecast eGFR value, and the composite regression forecast eGFR value is outside of the predetermined limits, evoking an action corresponding to treatment of the patient.

Embodiment 2: The method of claim 1, wherein the action evoked comprises at least one of initiating a signal that causes an alert to be presented to a clinician; initiating a signal that indicates a pattern of care to be initiated for the patient, and automatically scheduling a caregiver to initiate vascular access placement for the patient.

Embodiment 3: The method of claim 1 or 2, wherein the one or more physiologic variables comprises at least one of a measured uric acid value for the patient, a measured cystatin C value for the patient, and a measured serial serum creatinine for the patient.

Embodiment 4: The method of any of claims 1-3, wherein the plurality of time-stamped data points comprises at least three time-stamped data points.

Embodiment 5: The method of any of claims 1-4, wherein the one or more evolutionary algorithms comprises at least one of particular swarm optimization and differential evolution.

Embodiment 6: The method of any of claims 1-5, wherein the plurality of previously determined eGFRs are provided by an electronic health record (EHR) computer system.

Embodiment 7: The method of any of claims 1-6, wherein the future eGFR value for the time interval is used to predict a state of renal function for the patient.

Embodiment 8: The method of any of claims 1-7, wherein the future eGFR value for the time interval is used to predict when a need for dialysis for the patient is expected to begin.

Embodiment 9: The method of any of claims 1-8, wherein outside of predetermined limits comprises the future eGFR value being less than 15 ml/min/1.73 m$^2$ for the patient.

Embodiment 10: The method of any of claims 1-9, wherein the future eGFR value is used to determine a progression of at least one of chronic kidney disease; acute decompensation of renal function exacerbating chronic kidney disease; and infection superimposed upon chronic kidney disease.

Embodiment 11: One or more computer-readable media having computer-executable instructions embodied thereon that, when executed, facilitate a method for predicting candidacy for vascular access placement in a patient in stage four chronic kidney disease, the method comprising computing a current estimated glomerular filtration rate (eGFR) from one or more physiologic variables of the patient; receiving a plurality of previously determined eGFRs for the patient corresponding to a plurality of time-stamped data points; and determining if a future eGFR value for the patient at a future time interval is outside of predetermined limits by determining an eGFR slope value from the current eGFR and the plurality of previously determined eGFRs, computing a first logistic regression forecast eGFR value using the current eGFR, the plurality of previously determined eGFRs, and the eGFR slope value, minimizing an objective function using one or more evolutionary algorithms to compute a second logistic regression forecast eGFR value using the current eGFR, the plurality of previously determined eGFRs, and the eGFR slope value, combining at least the first logistic regression forecast eGFR value and the second logistic regression forecast eGFR value to compute a composite regression forecast eGFR value, determining if the composite regression forecast eGFR value is outside of predetermined limits, and upon determining that the composite regression forecast eGFR value is outside of predetermined limits, evoking an action corresponding to treatment of the patient.

Embodiment 12: The computer-readable media of claim 11, wherein the action evoked comprises at least one of initiating a signal that causes an alert to be presented to a clinician; initiating a signal for a plan of care to be initiated for the patient; and automatically scheduling a caregiver to initiate vascular access placement for the patient.

Embodiment 13: The computer-readable media of claim 11 or 12, wherein the one or more physiologic variables comprises at least one of a measured uric acid value for the patient, a measured cystatin C value for the patient, and a measured serial serum creatinine for the patient.

Embodiment 14: The computer-readable media of any of claims 11-13, wherein the one or more evolutionary algorithms comprises at least one of particular swarm optimization and differential evolution, and wherein the plurality of time-stamped data points comprises at least three time-stamped data points.

Embodiment 15: The computer-readable media of any of claims 11-14, wherein the plurality of previously determined eGFR values are provided by an electronic health record (EHR) computer system.

Embodiment 16: The computer-readable media of any of claims 11-15, wherein the future eGFR value for the future time interval is used to predict when a need for dialysis for the patient is expected to begin, and wherein outside of predetermined limits comprises the future eGFR value being less than 15 ml/min/1.73 m$^2$ for the patient.

Embodiment 17: The computer-readable media of any of claims 11-16, wherein the future eGFR value is used to determine a progression of at least one of chronic kidney disease; acute decompensation of renal function exacerbating chronic kidney disease; and infection superimposed upon chronic kidney disease.

Embodiment 18: A system for predicting candidacy for vascular access placement in a patient in stage four chronic kidney disease, the system comprising one or more processors; one or more sensors configured to measure one or more physiologic variables used to determine a current estimated glomerular filtration rate (eGFR) for the patient; and computer storage memory having computer-executable instructions stored thereon which, when executed by the processor, implement a method of computing a current eGFR from the one or more measured physiologic variables of the patient; receiving a plurality of previously determined eGFRs for the patient corresponding to a plurality of time-stamped data points; and determining a future eGFR value for the patient at a future time interval by determining an eGFR slope value from the current eGFR and the plurality of previously determined eGFRs, computing a first logistic regression forecast eGFR value using the current eGFR, the plurality of previously determined eGFRs, and the eGFR slope value, minimizing an objective function using one or more evolutionary algorithms to compute a second logistic regression forecast eGFR value using the current eGFR, the plurality of previously determined eGFRs, and the eGFR slope value, combining at least the first logistic regression forecast eGFR value and the second logistic regression forecast eGFR value to compute a composite regression forecast eGFR value, determining if the composite regression forecast eGFR value is outside of predetermined limits, and upon determining that the composite regression forecast eGFR value is outside of predetermined limits, evoking an action corresponding to treatment of the patient.

Embodiment 19: The system of claim 18, wherein the action evoked comprises at least one of initiating a signal that causes an alert to be presented to a clinician; initiating a signal for a plan of care to be initiated for the patient; automatically scheduling a caregiver to initiate vascular access placement for the patient; and modifying or generating a healthcare computer program for treating the patient.

Embodiment 20: The system of any of claims 18-19, wherein the one or more physiologic variables comprises at least one of a measured uric acid value for the patient, a measured cystatin C value for the patient, and a measured serial serum creatinine for the patient, and wherein the one or more evolutionary algorithms comprises at least one of particular swarm optimization and differential evolution, and wherein the plurality of time-stamped data points comprises at least three time-stamped data points.

From the foregoing, it will be seen that the technology described in this disclosure is well adapted to attain all the ends and objects hereinabove set forth together with other advantages which are obvious and which are inherent to the structure. It will be understood that certain features and sub-combinations are of utility and may be employed without reference to other features and sub-combinations. This is contemplated by and is within the scope of the claims. Since many possible aspects of the technology are possible without departing from the scope thereof, it is to be understood that all matter herein set forth or shown herein and in the accompanying drawings is to be interpreted as illustrative and non-limiting.

What is claimed is:

1. A method for device placement, the method comprising:
   collecting each of:
      a current estimated glomerular filtration rate (eGFR) for a patient calculated from one or more physiologic variables measured for the patient at or after a first time; and
      a plurality of previously determined eGFRs based at least partially on measurements: taken for the patient prior to the first time and corresponding to a plurality of time-stamped data points;
   determining a successive set of logistic regression forecast eGFR values comprising a first logistic regression forecast eGFR value and a second logistic regression forecast eGFR value, the successive set of logistic regression forecast eGFR values based on:
      the current eGFR; and
      the plurality of previously determined eGFRs;
   generating a composite regression forecast eGFR value by combining at least the first logistic regression forecast eGFR value and the second logistic regression forecast eGFR value; detecting that at least one of the composite regression forecast eGFR value, the first logistic regression forecast eGFR value, or the second logistic regression forecast eGFR value is outside of a predetermined limit; and
   in response to the detecting, identifying the patient as a candidate for placement of a device that facilitates vascular access;
   wherein:
      the predetermined limit is configured to facilitate identification of a patient candidacy for vascular access placement; and
      the device is placed in the patient for the vascular access based on the identifying.

2. The method of claim 1, wherein the first logistic regression forecast eGFR value is generated using:
   the current eGFR,
   the plurality of previously determined eGFRs, and
   an eGFR slope value calculated from a time series of the current eGFR and the plurality of previously determined eGFRs.

3. The method of claim 2, wherein the second logistic regression forecast eGFR value is generated using an evolutionary algorithm to minimize an objective function including the current eGFR, the plurality of previously determined eGFRs, and the eGFR slope value.

4. The method of claim 1, further comprising one or more of:
   initiating a signal that causes an alert to be presented to a clinician;
   initiating a signal that indicates a pattern of care to be initiated for the patient; or
   automatically scheduling a caregiver to initiate vascular access placement for the patient.

5. The method of claim 1, wherein the one or more physiologic variables comprise one or more of a measured uric acid value for the patient, a measured cystatin C value for the patient, or a measured serial serum creatinine for the patient.

6. The method of claim 1, wherein the plurality of time-stamped data points comprise at least three time-stamped data points.

7. The method of claim 1, wherein the generating is based on an evolutionary algorithm that comprises at least one of particular swarm optimization or differential evolution.

8. The method of claim 1, wherein the plurality of previously determined eGFRs are extracted from an electronic health record (EHR) computer system.

9. The method of claim 1, wherein a future eGFR value for a time interval is used to predict a state of renal function for the patient.

10. The method of claim 1, wherein a future eGFR value for a time interval is used to predict when a need for dialysis for the patient is expected to begin.

11. The method of claim 1, wherein outside of predetermined limits corresponds to a future eGFR value being less than 15 ml/min/1.73 m$^2$ for the patient.

12. The method of claim 1, wherein a future eGFR value is used to determine a progression of one or more of:
   chronic kidney disease;
   acute decompensation of renal function exacerbating chronic kidney disease; or
   infection superimposed upon chronic kidney disease.

13. The method of claim 1, wherein the second logistic regression forecast eGFR value is determined subsequent to determination of the first logistic regression forecast eGFR value.

14. One or more computer-readable media storing instructions that, when executed by one or more processors, cause initiation of operations comprising:
   collecting each of:
      a current estimated glomerular filtration rate (eGFR) for a patient calculated from one or more physiologic variables measured for the patient at or after a first time; and
      a plurality of previously determined eGFRs based at least partially on measurements: taken for the patient prior to the first time and corresponding to a plurality of time-stamped data points;
   determining a successive set of logistic regression forecast eGFR values comprising a first logistic regression forecast eGFR value and a second logistic regression forecast eGFR value, the successive set of logistic regression forecast eGFR values based on:
      the current eGFR; and
      the plurality of previously determined eGFRs;
   generating a composite regression forecast eGFR value by combining at least the first logistic regression forecast eGFR value and the second logistic regression forecast eGFR value; detecting that at least one of the composite regression forecast eGFR value, the first logistic regression forecast eGFR value, or the second logistic regression forecast eGFR value is outside of a predetermined limit; and
   in response to the detecting, identifying the patient as a candidate for placement of a device that facilitates vascular access;

wherein:
the predetermined limit is configured to facilitate identification of a patient candidacy for vascular access placement; and
the device is placed in the patient for the vascular access based on the identifying.

15. The one or more computer-readable media of claim 14, wherein the first logistic regression forecast eGFR value is generated using the current eGFR, the plurality of previously determined eGFRs, and an eGFR slope value calculated from a time series of the current eGFR and the plurality of previously determined eGFRs.

16. The one or more computer-readable media of claim 15, wherein the second logistic regression forecast eGFR value is generated using an evolutionary algorithm to minimize an objective function including the current eGFR, the plurality of previously determined eGFRs, and the eGFR slope value.

17. The one or more computer-readable media of claim 14, wherein the operations further comprise one or more of:
initiating a signal that causes an alert to be presented to a clinician;
initiating a signal for a plan of care to be initiated for the patient; or
automatically scheduling a caregiver to initiate vascular access placement for the patient.

18. The one or more computer-readable media of claim 14, wherein the patient is associated with a stage four chronic kidney disease diagnosis.

19. A system for device placement, the system comprising one or more processors and a memory storing instructions which, when executed by the one or more processors, cause initiation of operations comprising:
collecting each of:
a current estimated glomerular filtration rate (eGFR) for a patient calculated from one or more physiologic variables measured for the patient at or after a first time; and
a plurality of previously determined eGFRs based at least partially on measurements: taken for the patient prior to the first time and corresponding to a plurality of time-stamped data points;
determining a successive set of logistic regression forecast eGFR values comprising a first logistic regression forecast eGFR value and a second logistic regression forecast eGFR value, the successive set of logistic regression forecast eGFR values based on:
the current eGFR; and
the plurality of previously determined eGFRs;
generating a composite regression forecast eGFR value by combining at least the first logistic regression forecast eGFR value and the second logistic regression forecast eGFR value; detecting that at least one of the composite regression forecast eGFR value, the first logistic regression forecast eGFR value, or the second logistic regression forecast eGFR value is outside of a predetermined limit; and
in response to the detecting, identifying the patient as a candidate for placement of a device that facilitates vascular access;
wherein:
the predetermined limit is configured to facilitate identification of a patient candidacy for vascular access placement; and
the device is placed in the patient for the vascular access based on the identifying.

20. The system of claim 19, further comprising one or more sensors configured to measure the one or more physiologic variables, wherein the first logistic regression forecast eGFR value is generated using the current eGFR, the plurality of previously determined eGFRs, and an eGFR slope value calculated from a time series of the current eGFR and the plurality of previously determined eGFRs.

21. The system of claim 20, wherein the second logistic regression forecast eGFR value is generated using an evolutionary algorithm to minimize an objective function including the current eGFR, the plurality of previously determined eGFRs, and the eGFR slope value.

22. The system of claim 19, wherein the one or more physiologic variables comprise one or more of a measured uric acid value for the patient, a measured cystatin C value for the patient, or a measured serial serum creatinine for the patient, wherein the generating is based on an evolutionary algorithm that comprises at least one of particular swarm optimization or differential evolution, and wherein the plurality of time-stamped data points comprises at least three time-stamped data points.

23. The system of claim 19, wherein the patient is associated with a stage four chronic kidney disease diagnosis.

* * * * *